United States Patent [19]

Hoelderich et al.

[11] Patent Number: 4,743,702

[45] Date of Patent: May 10, 1988

[54] PREPARATION OF ALIPHATIC DINITRILES

[75] Inventors: Wolfgang Hoelderich, Frankenthal; Hubert Lendle, Ludwigshafen; Peter Magnussen, Bad Durkheim; Hans Leitner, Frankenthal; Jost H. Manegold, Lambsheim; Wolfgang Leitenberger, Mannheim, all of Fed. Rep. of Germany

[73] Assignee: BASF Aktiengesellschaft, Ludwigshafen, Fed. Rep. of Germany

[21] Appl. No.: 839,161

[22] Filed: Mar. 13, 1986

[30] Foreign Application Priority Data

Mar. 26, 1985 [DE] Fed. Rep. of Germany ....... 3510876

[51] Int. Cl.$^4$ ............................................. C07C 120/08
[52] U.S. Cl. ..................................... 558/311; 558/312
[58] Field of Search ................................. 558/311, 312

[56] References Cited

U.S. PATENT DOCUMENTS 3,324,165 6/1967 Baer et al. ..................... 502/247 X
4,315,869 2/1982 Merger et al. .................. 546/246 X

FOREIGN PATENT DOCUMENTS 1284139 2/1972 United Kingdom .
1397729 6/1975 United Kingdom .

OTHER PUBLICATIONS

Rao et al.; Chemistry and Industry, (1984), p. 270.
Kokotailo et al.; Chem. Soc. Spec. Publ. (1980), vol. 33, pp. 133–139.
Jacobs et al.; Zeolites, (1981), vol. 1, pp. 161–168.
Chemical Abstracts, 84, (1976), 84:4433a, Costa et al.
The Merck Index; 10th ed., (1983), p. 1454 [listing No. 9922].
Hawley; "The Condensed Chemical Dictionary", 10th ed., (1981); pp. 1105–1106, Van Nostrand, N.Y.

*Primary Examiner*—Joseph Paul Brust
*Attorney, Agent, or Firm*—Keil & Weinkauf

[57] ABSTRACT

Aliphatic dinitriles are prepared by reacting aliphatic dicarboxylic acids with ammonia in excess at from 200° to 500° C. in the presence of zeolites as catalysts.

9 Claims, No Drawings

PREPARATION OF ALIPHATIC DINITRILES

A widely practised industrial process for preparing aliphatic dinitriles comprises reacting aliphatic dicarboxylic acids with ammonia in the presence of catalysts, for example in a fluidized catalyst bed. Suitable catalysts are water-attracting agents, such as silica gel, boron phosphate, alumina or mixtures thereof, which can be activated by small amounts of alkali metal oxide and addition of acid substances, such as phosphoric acid, boric acid, vanadic acid, molybdic acid, tungstic acid or other heteropolyacids, as is known from German Laid-Open Applications Nos. DOS 1,188,578 and DOS 2,056,295. The known processes have the disadvantage that the catalysts quickly become deactivated and lose their selectivity. On account of the frequently necessary catalyst regeneration at high temperatures, for example amorphous silicon dioxide recrystallizes to cristobalite. This causes irreversible damage to the catalyst. These disadvantages also apply to catalysts in which phosphoric acid is present in less than stoichiometric equivalents compared with the alkali metal content of the silicon dioxide carrier, which are known from German Laid-Open Application No. DOS 2,056,295.

It is an object of the present invention to provide a process for preparing aliphatic dinitriles by reacting aliphatic diacarboxylic acids and ammonia, wherein the catalysts used have a high selectivity and long life and can be easily regenerated without loss of activity or selectivity and few byproducts are formed.

We have found that this object is achieved in a process for preparing aliphatic dinitriles by reacting aliphatic dicarboxylic acids with ammonia in excess at from 200 to 500° C. in the presence of catalysts, wherein the catalysts used are zeolites.

The novel process has the advantage that the catalysts can be easily regenerated and have a high activity and selectivity even after repeated regeneration. The novel process further has the advantage that a very high selectivity is obtained.

Preferred aliphatic dicarboxylic acid starting materials have the formula (I) HOOC—R—COOH in which R is an aliphatic radical of 2 to 12 carbon atoms. In preferred starting materials of the formula I, R is alkylene of 2 to 12, in particular 2 to 8, carbon atoms. Suitable dicarboxylic acids are for example succinic acid, glutaric acid, α-methylglutaric acid, adipic acid, azelaic acid or sebacic acid. Particular industrial importance has been attained by adipic acid.

The reaction is carried out with excess ammonia. Advantageously from 4 to 20, in particular from 6 to 12, moles of ammonia are used per mole of dicarboxylic acid.

The reaction can be carried out in the gas phase or in the liquid phase, for example in the presence of diluents such as the dinitrile produced in each case. The reaction is advantageously carried out in the gas phase.

In general the reaction is carried out at from 200° to 500° C. If the reaction is carried out in the liquid phase, temperatures of from 250° to 350° C., in particular from 280° to 330° C., have proved suitable. If the reaction is carried out in the gas phase, it is advantageous to employ temperatures of from 300° to 500° C., in particular from 350° to 420° C.

According to the invention, the catalysts used are zeolites. Zeolites are crystalline aluminosilicates which have a highly ordered structure with a rigid three-dimensional network of $SiO_4$ and $AlO_4$ tetrahedra which are connected by shared oxygen atoms. The ratio of silicon and aluminum atoms to oxygen is 1:2. The electro-valence of the aluminum-containing tetrahedra is neutralized by inclusion of cations, for example an alkali metal or hydrogen atom, in the crystal. An exchange of cations is possible. The spaces between the tetrahedra are occupied before the dehydration through drying or calcination by water molecules. Instead of the aluminum the zeolites can also contain trivalent elements, such as boron, gallium, iron or chromium, and in place of the silicon tetravalent elements such as germanium, titanium, zirconium or hafnium.

The catalysts used are preferably zeolites of the pentasil type. These zeolites can have different chemical compositions. They are aluminosilicate, borosilicate and iron, gallium, chromium, arsenic or bismuth silicate zeolites or mixtures thereof and aluminogermanate, borogermanate and gallium or iron germanate zeolites or mixtures thereof. Particular preference is given to borosilicate and iron silicate zeolites of the pentasil type.

The borosilicate zeolite is prepared for example at from 90° to 200° C. under autogenous pressure by reacting a boron compound, such as boric acid, with a silicon compound, preferably with finely divided silicon dioxide, in aqueous amine solution, in particular in 1,6-hexanediamine or 1,3-propanediamine or triethylenetetramine solution, with or without added alkali or alkaline earth metal. In place of an aqueous amine solution it is also possible to use a solution in ether, for example in diethylene glycol dimethyl ether, or an alcoholic solution, for example in 1,6-hexanediol.

The iron silicate zeolite is obtained for example from an iron(III) salt, preferably iron(III) sulfate, and a silicon compound, preferably finely divided silicon dioxide, in aqueous amine solution, in particular in 1,6-hexanediamine with or without added alkali or alkaline earth metal at from 100° to 200° C. under autogenous pressure.

The borosilicate and iron silicate zeolites thus prepared are isolated and dried at from 100° to 160° C., preferably 110° C., and calcined at from 450° to 550° C., preferably from 500° to 540° C., and are, advantageously immediately thereafter, molded into extrudates or fluidizable material. The molding can for example also be effected with a binder in a ratio of from 95:5 to 30:70. Suitable binders are silicon dioxide, preferably silica gel, silica sol or finely divided silicon dioxide, finely divided titanium dioxide, amorphous aluminosilicates having a ratio of silicon dioxide to aluminum oxide such as from 25:70 to 95:5, and aluminum oxides.

After the molding, the extrudates, the pellets or the fluidizable material are for example dried at 110° C. for 16 hours and calcined at 500° C. for 16 hours. A particularly advantageous way of preparing these catalysts is to mold the isolated borosilicate or iron silicate zeolite immediately after drying and only then to calcine it. The catalysts which have been converted into extrudates can be for example milled and sieved to give fluidizable material having a particle size of from 0.05 to 0.5 mm.

If from the manner of preparation the zeolite is not in the catalytically preferred acidic H form, but for example in the Na form, then the latter can be converted by ion exchange for ammonium ions and subsequent calcination or by treatment with acids completely or partially into the desired H form. To increase the selectivity, the time-on-stream and the number of regenerations, the zeolites can also be variously modified, for example by ion-exchanging or impregnating the unmolded or molded zeolite with alkali metals such as sodium nitrate, unless the alkali metal form of the zeolite is already present from the synthesis, with alkaline earth metals such as calcium or magnesium, with earth metals such as boron or tallium, with transition metals such as molybedenum, tungsten, iron, zinc or copper, with noble metals such as palladium or rare earths such as cerium or lanthanum in the form of their salts.

Advantageously such modified zeolites are prepared by presenting the molded pentasil zeolites in a rising pipe and, at from 20° to 100° C., passing for example an aqueous solution of a halide or nitrate of the abovementioned metals thereover. Such an ion exchange can be carried out for example on the hydrogen, ammonium or alkali metal form of the zeolite. Metal can also be applied to the zeolite for example by impregnating the zeolitic material for example with a halide, a nitrate or an oxide of the abovementioned metals in aqueous or alcoholic solution. Both ion exchange and impregnation are followed by not less than one drying and, if desired, a further calcination.

In the case of zeolites which are doped with metals such as palladium or platinum an aftertreatment with hydrogen is advantageous.

A further way of modifying the zeolites comprises subjecting them, molded or unmolded, to a treatment with acids such as phosphoric acid, hydrochloric acid or hydrofluoric acid and/or with steam. Advantageously, for example, the zeolites are treated in powder form at 80° C. with 1N phosphoric acid for 1 hour. The treatment is followed by washing with water, drying at 110° C. for 16 hours and calcining at 500° C. for 20 hours. Alternatively, zeolites are treated before or after molding with binders for example at from 60° to 80° C. with 3–25% by weight strength, in particular 12–20% by weight strength, aqueous hydrochloric acid for from 1 to 3 hours. Afterwards the zeolite thus treated is washed with water, is dried at from 100° to 160° C. and is calcined at from 400° to 500° C.

Zeolites can also be modified by applying phosphorus compounds, such as trimethoxy phosphate, or primary, secondary or tertiary sodium phosphate. The treatment with primary sodium phosphate has been found to be particularly advantageous. It comprises impregnating the zeolites in extrudate, tablet or fluidizable form with aqueous $NaH_2PO_4$ solution, drying at 110° C. and calcining at 500° C.

If the zeolite catalysts become deactivated, which in the process according to the invention can occur due to carbonization, the catalysts are simple to regenerate back to their initial activity by burning off the carbon deposit with air or with a mixture of air and nitrogen at from 400° to 550° C., preferably from 500° to 540° C. Partial carbonization can also be used to set the activity of the catalyst to peak selectivity for the desired reaction product. If the reaction of the dicarboxylic acid with ammonia is carried out in the presence of gases such as hydrogen, nitrogen or steam, this can be used to affect the product composition and the catalyst life.

In general, the catalysts are used as extrudates of from 2 to 4 mm in length, as tablets of from 3 to 5 mm in diameter or as fluidizable material having a particle size of from 0.05 to 0.5 mm, as preferred. The fluidizable material can be prepared by comminuting extrudates and sieving or by spray-drying.

Advantageously the reaction is carried out in a fluidized catalyst bed by passing in from below gaseous ammonia and supplying the dicarboxylic acid as a vapor or vaporizing it in the fluidized bed. Alternatively, the reaction can also be carried out over a fixed-bed catalyst or in liquid phase with suspended catalyst.

Dinitriles prepared by the process of the invention are suitable for preparing diamines which are starting materials for nylons.

The process according to the invention is illustrated by the Examples below.

The catalyst A used in the Examples is prepared as follows:

CATALYST A

The zeolite was prepared in a hydrothermal synthesis from 640 g of $SiO_2$ (finely divided silica), 122 g of $H_3BO_3$, 800 g of an aqueous hexanediamine solution (mixture 50:50% by weight) at 170° C. under autogenous pressure in a stirred autoclave. After filtration and washing, the crystalline reaction product was dried at 100° C. for 24 hours and calcined at 500° C. for the same time. This gave a borosilicate zeolite of the pentasil type, which contained 94.2% by weight of $SiO_2$ and 2.3% by weight of $B_2O_3$. This zeolite powder is molded with silica gel in a weight ratio of 90:10 to 5 mm extrudates, which are dried at 110° C. for 16 hours. These extrudates are reduced in size to fluidizable material having a sieve fraction of from 50 to 500μ. This is followed by calcination at 500° C. for 16 hours. 600 g of this fluidizable material are impregnated with a solution of 283 g of $NaH_2PO_4.H_2O$ in 500 g of $H_2O$ and are then dried at 110° C. and calcined at 500° C. for 14 hours. Catalyst A contains 7.6% by weight of P and 5.6% by weight of Na.

EXAMPLE I 500 g of catalyst A with particle diameters of from 0.06 mm to 0.3 mm are fitted into a fluidized bed reactor of 60 mm in internal diameter and are heated to 350° C. in a fluidizing stream of 300 liters (S.T.P.) per hour of ammonia. Adipic acid flakes (1000 g) are metered via a rotary feeder at a rate of 200 g per hour into a 100 liters (S.T.P.) per hour conveying gas stream ($NH_3$) and are conveyed into the bottom quarter of the fluidized bed. The reaction products are isolated from the reaction gas by condensation to gas temperatures of about 0° C. The phases which form are freed of dissolved ammonia by stripping with $N_2$, are separated from each other, are weighed and are analyzed by GC. The following yields are obtained:

| | |
|---|---|
| adiponitrile | 87.4% (mol/mol) |
| cyanovaleric acid | 1.5% (mol/mol) |
| cyanovaleriamide | 7.1% (mol/mol) |
| Σ useful products | 96.0% (mol/mol) |
| cyanocyclopentanoneimine | 1.1% (mol/mol) |
| cyclopentanone | 1.0% (mol/mol) |
| | 98.1% (mol/mol) |

EXAMPLE II

Example I is repeated, except that a temperature of 400° C. is used, affording:

| | |
|---|---|
| adiponitrile | 94% (mol/mol) |
| cyanovaleric acid | 0.7% (mol/mol) |

| -continued | |
| --- | --- |
| cyanovaleriamide | 2.8% (mol/mol) |
| Σ useful products | 97.5% (mol/mol) |
| cyanocyclopentanoneimine | 0.5% (mol/mol) |
| cyclopentanone | 0.9% (mol/mol) |
| | 98.9% (mol/mol) |

EXAMPLE III

Example I is repeated, except that a temperature of 420° C. is used, affording:

| | |
| --- | --- |
| adiponitrile | 94.8% (mol/mol) |
| cyanovaleric acid | 0.4% (mol/mol) |
| cyanovaleriamide | 1.2% (mol/mol) |
| Σ useful products | 96.4% (mol/mol) |
| cyanocyclopentanoneimine | 1.1% (mol/mol) |
| cyclopentanone | 0.8% (mol/mol) |
| | 98.3% (mol/mol) |

CATALYST B

The fluidizable material described in the case of catalyst A is then doped with $O=P(OCH_3)_3$ (trimethoxyphosphate) in place of sodium dihydrogenphosphate. 600 g of the fluidizable material are impregnated with a mixture of 287 g of $O=P(OCH_3)_3$ and 360 g of $H_2O$, and are then dried at 150° C. and calcined at 500° C. for 14 hours. The phosphorus content of catalyst B is 2.16%.

EXAMPLE IV

Example I is repeated, except that the reaction is carried out at 410° C. using catalyst B in place of A. The following results are obtained:

| | |
| --- | --- |
| adiponitrile | 86.2% (mol/mol) |
| cyanovaleric acid | 0.4% (mol/mol) |
| cyanovaleriamide | 2.0% (mol/mol) |
| Σ useful products | 88.6% (mol/mol) |
| cyanocyclopentanoneimine | 2.4% (mol/mol) |
| cyclopentanone | 3.2% (mol/mol) |
| | 94.2% (mol/mol) |

COMPARATIVE EXAMPLE

Example I is repeated, except that $SiO_2$ is used as catalyst and a temperature of 480° C. is maintained. The following results are obtained:

| | |
| --- | --- |
| adiponitrile | 83.4% (mol/mol) |
| cyanovaleric acid | 3.0% (mol/mol) |
| cyanovaleriamide | 0.6% (mol/mol) |
| Σ useful products | 87.0% (mol/mol) |
| cyanocyclopentanoneimine | 2.4% (mol/mol) |
| cyclopentanone | 4.3% (mol/mol) |

We claim:

1. A process for preparing a $C_2$–$C_{12}$ alkylenedinitrile which comprises:
   reacting a $C_2$–$C_{12}$ alkylenedicarboxylic acid with excess ammonia at from 200° to 500° C. in the presence of a zeolite having a pentasil structure selected from the group consisting of borosilicate and iron silicate.

2. The process of claim 1, wherein the zeolite having a pentasil structure is a borosilicate.

3. The process of claim 2, wherein the alkylenedinitrile is adipodinitrile and the alkylenedicarboxylic acid is adipic acid.

4. The process of claim 1, wherein the zeolite having a pentasil structure is modified by applying a phosphorous compound.

5. The process of claim 2, wherein the zeolite having a pentasil structure is modified by applying a phosphorous compound.

6. The process of claim 3, wherein the zeolite having a pentasil structure is modified by applying a phosphorous compound.

7. The process of claim 1, wherein the zeolite having a pentasil structure is modified by applying alkali metal ions.

8. The process of claim 2, wherein the zeolite having a pentasil structure is modified by applying alkali metal ions.

9. The process of claim 3, wherein the zeolite having a pentasil structure is modified by applying alkali metal ions.

* * * * *